March 18, 1941. W. I. JOHNSTON Plant Pat. 461
ROSE PLANT
Filed Nov. 1, 1940
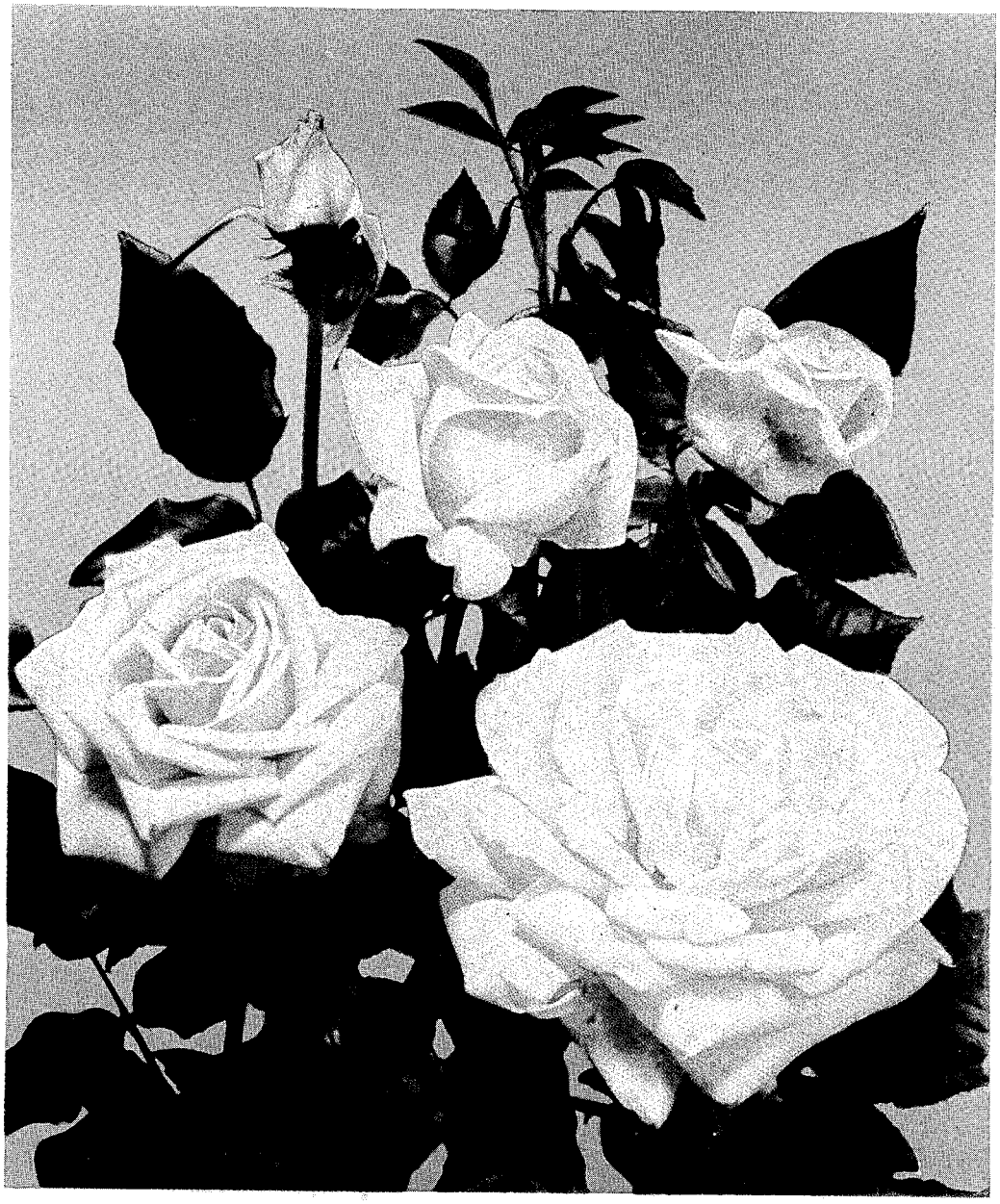
INVENTOR
W. I. Johnston
By Robert Cobb
ATTORNEYS.

Patented Mar. 18, 1941

Plant Pat. 461

UNITED STATES PATENT OFFICE

461

ROSE PLANT

Walter Irwin Johnston, Portadown, Ireland, assignor to Jackson & Perkins Company, Newark, N. Y.

Application November 1, 1940, Serial No. 363,952

1 Claim. (Cl. 47—61)

The present invention relates to a new and distinct variety of hybrid tea rose plant, the result of a cross of the well known variety Mrs. Sam McGredy and an unnamed seedling.

This new variety is characterized as to novelty, generally speaking, by its compact form of growth, freedom of blooming, the globular shape of the flowers, retained to the end, and unusual combination of coloring of said flowers.

More specifically, the flower of this new rose is distinctive because of its Capucine Yellow color overlaid with Grenadine Pink when first opening, developing delightfully through Bittersweet Orange with Grenadine Pink to light Orange Yellow tinged with Grenadine Pink in the full blown rose.

Another feature of novelty is found in the color of the peduncle, Light Cress Green overlaid with Madder Brown, and in the color combination of the foliage. With respect to the latter, the color of the intermediary foliage on blooming stems is Dark Cress Green with characteristic Madder Brown veining and edging, maturing into large shiny leathery Dark Cress Green foliage. The new foliage is characterized by the Burnt Lake color of the upper side and Victoria Lake color of the lower side.

The new variety has been asexually reproduced and its novel characteristics have been found to come true to form.

The following is a detailed description of the new variety, all color terminology being in accord with Ridgway's Color Standard:

Parentage:

*Seed parent.*—Mrs. Sam McGredy.

*Pollen parent.*—Unnamed seedling.

Classification: Botanic and commercial—hybrid tea.

*Flower*

(Observations made in fields and gardens of Jackson & Perkins Company, Newark, New York, in the morning of June 21, 1940.)

Blooming habit: Recurrent—continuous.

Bud:

*Size.*—Large.

*Form.*—Globular. Is not affected by wet or hot weather.

*Color.*—When sepals first divide—Grenadine Red, Plate II. When petals begin to unfurl—Grenadine Red, Plate II, top, shading to Orange, Plate III, toward base. When half blown: inside of petals—Bittersweet Orange, Plate II, overlaid with Grenadine Pink, Plate II. Reverse of petals—Deep Chrome, Plate III, deepening toward edges to Grenadine Red, Plate II.

*Sepals.*—Serrated, branched, "hood" above bud. Curl back when petals unfold. *Color*: outside, Cress Green, Plate XXXI. Inside, Pale Lumiere Green, Plate XXXI.

*Calyx.*—*Shape*—apple. *Size*—broad. *Aspect*—smooth. *Color*—Cress Green, Plate XXXI.

*Peduncle.*—*Length*—long. *Aspect*—prickly. *Color*—Light Cress Green, Plate XXXI overlaid with Madder Brown, Plate XIII. *Strength*—stiff; heavy.

*Opening.*—Bud opens well. Is not affected by adverse conditions.

Bloom:

*Size.*—Large. Average size when fully expanded—5 inches.

*Borne.*—Several together.

*Stems.*—Medium length; strong.

*Form.*—When first open—globular. Permanence—retains its form to the end.

*Petalage.*—Double (full but open center). Number of petals under normal conditions—35.

*Color.*—Center of flower—Capucine Yellow, Plate III overlaid with Grenadine Pink, Plate II. Outer petals—Orange Buff, Plate III tinged with Grenadine Pink, Plate II. Base of petals (aiglet)—Lemon Chrome, Plate IV. Inside of petals—Deep Chrome, Plate III, overlaid with Grenadine Pink, Plate II. Reverse of petals—Orange Buff, Plate III, tinged with Grenadine Pink, Plate II. General tonality from a distance—Capucine Yellow, Plate III.

*Discoloration.*—General tonality at end of first day—Bittersweet Orange, Plate II, tinged with Grenadine Pink, Plate II. Second day—Orange Buff, Plate II, tinged with Grenadine Pink, Plate II. Third day—Light Orange Yellow, Plate III, tinged with Grenadine Pink, Plate II.

Petals:

*Texture.*—Thick. Is not affected by wet or hot weather.

*Appearance.*—Inside—satiny. Outside—shiny.

*Form.*—Oval, slightly notched.

*Arrangement.*—Imbricated (regularly arranged shingle-like). *Petaloids in center*—few; large.

*Persistence.*—Drop off cleanly.

*Fragrance.*—Moderate. Nature—fruity (Russet apple).

*Lasting quality.*—On the plant and as cut flower—long.

Genital organs:

*Stamens, anthers.*—*Size*—medium; many. *Color*—Deep Chrome, Plate III. *Arrangement*—regular around styles.

*Stamens, filaments (threads).*—Long. *Color*—Apricot Yellow, Plate IV.

*Pollen.*—Deep Chrome, Plate III.
*Styles.*—Bunched, even; medium length; heavy.
*Stigmas.*—Apricot Yellow, Plate IV.
*Ovaries.*—All enclosed in calyx.

*Plant*

Form: Bush.
Growth: Vigorous; compact.
Foliage: 5 leaflets.
*Size.*—Large.
*Quantity.*—Normal.
*Color.*—*New foliage:* upper side—Burnt Lake, Plate XII; under side—Victoria Lake, Plate I. *Old foliage*: upper side—Dark Cress Green, Plate XXXI; under side—Cress Green, Plate XXXI. *Intermediary foliage*—Dark Cress Green, Plate XXXI, with Madder Brown, Plate XIII, edges and center rib. *Intermediary foliage*: leaf stem—Madder Brown, Plate XIII.
*Shape.*—Oval pointed.
*Texture.*—Upper side—leathery, glossy; under side—smooth. *Ribs and veins*—ordinary, light.
*Edge.*—Serrated (saw toothed).
*Serration.*—Single; small.
*Rachis.*—*Color*—Cress Green, Plate XXXI. Under side—prickles and hooks.
*Stipules.*—Short; bearded.
*Disease resistance.*—Resistant.
Wood:
*New wood.*—Cress Green, Plate XXXI, tinged with Madder Brown, Plate XIII. *Bark*—smooth.
*Old wood.*—Jade Green, Plate XXXI. *Bark*—smooth.
Thorns (thorns are divided into thorns, prickles and short needles):
*Thorns.*—*Quantity*—On main stalks from base and on laterals from stalk—ordinary. *Form*—broad base; medium length; hooked downward. *Color when young*—Madder Brown, Plate XIII. *Position*—irregular.
*Prickles.*—On main stalks—few. On laterals—few. *Color*—Pompeian Red, Plate XIII.
*Short needles.*—On main stalks—none. On laterals—none.

I claim:

A new and distinct variety of hybrid tea rose plant characterized as to novelty by its compact bush form, freedom of bloom, the distinctive color combination of both the bud and developed flowers, and color and texture of the foliage, substantially as shown and described.

WALTER IRWIN JOHNSTON.